US00PP17676P2

(12) United States Plant Patent
Takamura

(10) Patent No.: US PP17,676 P2
(45) Date of Patent: May 1, 2007

(54) ***VIOLA* PLANT NAMED 'SUNVIOBU'**

(50) Latin Name: *Viola cornuta*
Varietal Denomination: Subviobu

(75) Inventor: Naoto Takamura, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/259,305

(22) Filed: Oct. 26, 2005

(51) Int. Cl.
*A01H 5/00* (2006.01)

(52) U.S. Cl. ..... Plt./323

(58) Field of Classification Search ..... Plt./323
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Viola* plant named 'Sunviobu', characterized by its outwardly spreading and mounded plant habit; vigorous and freely branching growth habit; freely flowering habit; single violet-colored flowers with long peduncles; long flowering period; and good garden performance.

1 Drawing Sheet

Botanical designation: *Viola cornuta.*
Cultivar denomination: 'Sunviobu'.

BACKGROUND OF THE INVENTION

The present Invention relates to a new and distinct cultivar of *Viola* plant, botanically known as *Viola cornuta,* and hereinafter referred to by the cultivar name Sunviobu.

The new *Viola* is a product of a planned breeding program conducted by the Inventor in Higashiomi, Shiga, Japan. The objective of the breeding program is to create new *Violas* with numerous flowers with attractive flower colors.

The new *Viola* originated from a cross-pollination made by the Inventor in April, 2001, of a proprietary selection of *Viola cornuta* identified as code number 9V-38-1, not patented, as the female, or seed, parent with a proprietary selection of *Viola cornuta* identified as code number 0V-40-1, not patented, as the male, or pollen, parent. The new *Viola* was selected as a single plant from the resulting progeny of the cross-pollination by the Inventor in a controlled environment in Higashiomi, Shiga, Japan.

Asexual reproduction of the new cultivar by terminal cuttings in a controlled environment in Higashiomi, Shiga, Japan since April, 2003 has shown that the unique features of this new *Viola* are stable and reproduced true to type in successive generations.

SUMMARY OF THE INVENTION

Plants of the cultivar Sunviobu have not been observed under all possible environmental conditions. The phenotype may vary somewhat with variations in environment such as temperature and light intensity without, however, any variance in genotype.

The following traits have been repeatedly observed and are determined to be the unique characteristics of 'Sunviobu'. These characteristics in combination distinguish 'Sunviobu' as a new and distinct *Viola* cultivar:

1. Outwardly spreading and mounded plant habit.
2. Vigorous and freely branching growth habit.
3. Freely flowering habit.

4. Single violet-colored flowers with long peduncles.
5. Long flowering period.
6. Good garden performance.

Plants of the new *Viola* differ from plants of the female parent selection in the following characteristics:

1. Plants of the new *Viola* have smaller flowers than plants of the female parent selection.
2. Plants of the new *Viola* differ from plants of the female parent selection in flower color as plants of the female parent selection have pale yellow-colored flowers.

Plants of the new *Viola* differ from plants of the male parent selection in the following characteristics:

1. Plants of the new *Viola* are taller and narrower than plants of the male parent selection.
2. Plants of the new *Viola* and the male parent selection differ in flower color as plants of the male parent selection have yellow-colored flowers.

Plants of the new *Viola* can be compared to plants of the cultivar Alpine Summer, not patented. In side-by-side comparisons conducted in Higashiomi, Shiga, Japan, plants of the new *Viola* differed from plants of the cultivar Alpine Summer in the following characteristics:

1. Plants of the new *Viola* were taller than plants of the cultivar Alpine Summer.
2. Plants of the new *Viola* had longer leaves than plants of the cultivar Alpine Summer.
3. Plants of the new *Viola* had larger flowers than plants of the cultivar Alpine Summer.
4. Plants of the new *Viola* and the cultivar Alpine Summer differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Viola.*

The photograph at the top of the sheet comprises a side perspective view of a typical flowering plant of 'Sunviobu' grown in a container.

The photograph at the bottom of the sheet comprises a close-up view of typical flowers of 'Sunviobu'.

DETAILED BOTANICAL DESCRIPTION

The aforementioned photographs and following observations and measurements describe plants grown in Higashiomi, Shiga, Japan, in 15-cm containers for about seven months in an outdoor nursery during the spring with day temperatures about 13° C. and night temperatures about 3° C. Plants were pinched one time in the early spring. Color references are made to The Royal Horticultural Society Colour Chart, 2001 Edition, except where general terms of ordinary dictionary significance are used.

Botanical classification: *Viola cornuta* cultivar Sunviobu.

Parentage:

*Female, or seed, parent.*—Proprietary selection of *Viola cornuta* selection identified as code number 9V-38-1, not patented.

*Male, or pollen, parent.*—Proprietary selection of *Viola cornuta* selection identified as code number 0V-40-1, not patented.

Propagation:

*Type cutting.*—Terminal vegetative cuttings.

*Time to initiate roots.*—About two weeks at 20° C. to 25° C.

*Time to develop roots.*—About four weeks at 20° C. to 25° C.

*Root description.*—Fine, fibrous, fleshy; pale yellow in color.

*Rooting habit.*—Freely branching.

Plant description:

*Plant and growth habit.*—Annual flowering plant; outwardly spreading and mounded plant habit. Vigorous growth habit. Freely branching habit with about 80 lateral branches developing per plant.

*Plant height.*—About 20.8 cm.

*Plant diameter.*—About 52.4 cm.

*Lateral branches.*—Length: About 19 cm. Diameter: About 1.7 mm. Internode length: About 3 cm. Texture: Pubescent. Color: 144A.

*Foliage description.*—Arrangement: Alternate, simple. Length: About 3.2 cm. Width: About 1 cm. Shape: Narrowly elliptic. Apex: Rounded. Base: Obtuse. Margin: Crenate. Texture, upper and lower surfaces: Pubescent. Venation pattern: Pinnate; reticulate. Color: Developing and fully expanded foliage, upper surface: 137A. Developing and fully expanded foliage, lower surface: 146C. Venation, upper and lower surfaces: Similar to lamina. Petioles: Length: About 1 cm. Diameter: About 4 mm. Texture, upper and lower surfaces: Smooth, glabrous. Color, upper and lower surfaces: 144A. Stipules: Length: About 1.9 cm. Width: About 1.3 cm. Shape: Narrowly ovate. Apex: Obtuse. Base: Obtuse. Margin: Pinnately parted. Texture, upper and lower surfaces: Smooth, glabrous. Color, upper and lower surfaces: 137A.

Flower description:

*Flower type and habit.*—Single rotate flowers; flowers face mostly upward or outward; axillary. Flowers not persistent. Freely flowering habit; about 152 flowers and flower buds per plant.

*Natural flowering season.*—Long flowering period, plants flower from autumn through the spring in Japan; flowering continuous during this period.

*Flower longevity on the plant.*—About five to seven days.

*Fragrance.*—None detected.

*Flower diameter.*—About 3.2 cm by 3.1 cm.

*Flower length (depth).*—About 1.1 cm.

*Flower buds.*—Length: About 1.4 cm. Diameter: About 5 mm. Shape: Lenticular. Color: 99C.

*Corolla.*—Quantity/arrangement: Five petals; fused in a single whorl. Petal length: Upper petals: About 1.7 cm. Lateral petals: About 1.3 cm. Lower petal: About 1.4 cm. Petal width: Upper petals: About 1.9 cm. Lateral petals: About 1.3 cm. Lower petal: About 2.2 cm. Petal shape: Upper petals: Rounded with rounded apex. Lateral petals: Rounded with rounded apex. Lower petal: Cordate with cordate apex. Petal margin, all petals: Entire. Petal texture, all petals, upper and lower surfaces: Glabrous, smooth; velvety. Color: Upper petals, when developing, upper surface: 86A. Lateral petals, when developing, upper surface: 92A; towards the base, 155A with fine lines, N92C. Lower petal, when developing, upper surface: 92A; towards the base, 155A with fine lines, N92B; at base, 13A. Upper petals, when developing, lower surface: N88B. Lateral petals, when developing, lower surface: 94B. Lower petal, when developing, lower surface: 94B. Upper petals, fully developed, upper surface: Close to 86A. Lateral petals, fully developed, upper surface: 92A; towards the base, fine lines, N92C. Lower petal, fully developed, upper surface: 92A; towards the base, fine lines, N92B; at the base, 13A. Upper petals, fully developed, lower surface: N88B. Lateral petals, fully developed, lower surface: 94B. Lower petals, fully developed, lower surface: 94B.

*Spurs (lower petal only).*—Length: About 4.4 mm. Width: About 0.6 mm. Color: 94B.

*Sepals.*—Arrangement/appearance: Single whorl of five sepals fused at base; star-shaped calyx. Length: About 1.1 cm to 1.3 cm. Width: About 2.4 mm. Shape: Lanceolate. Apex: Acute. Margin: Entire. Color, upper and lower surfaces: 138A.

*Peduncles.*—Length: About 10.4 cm. Width: About 0.9 mm. Strength: Moderately strong. Texture: Smooth, glabrous. Color: 144A.

*Reproductive organs.*—Stamens: Quantity: Five per flower. Anther shape: Ellipsoidal. Anther size: About 1 mm by 0.7 mm. Anther color: 11D. Pollen amount: Moderate. Pollen color: 11D. Pistils: Quantity: One per flower. Pistil length: About 5 mm. Style length: About 0.6 mm. Style color: 2C. Stigma shape: Ellipsoidal. Stigma color: 144C. Ovary color: 144C.

*Seeds.*—Seed development has not been observed.

Disease/pest resistance: Plants of the new *Viola* have not been noted to be resistant to specific pathogens and pests common to *Viola*.

Garden performance: Plants of the new *Viola* have been observed to have good garden performance and tolerate rain, wind and tolerated temperatures from −7° C. to 25° C.

It is claimed:

1. A new and distinct cultivar of *Viola* plant named 'Sunviobu', as illustrated and described.

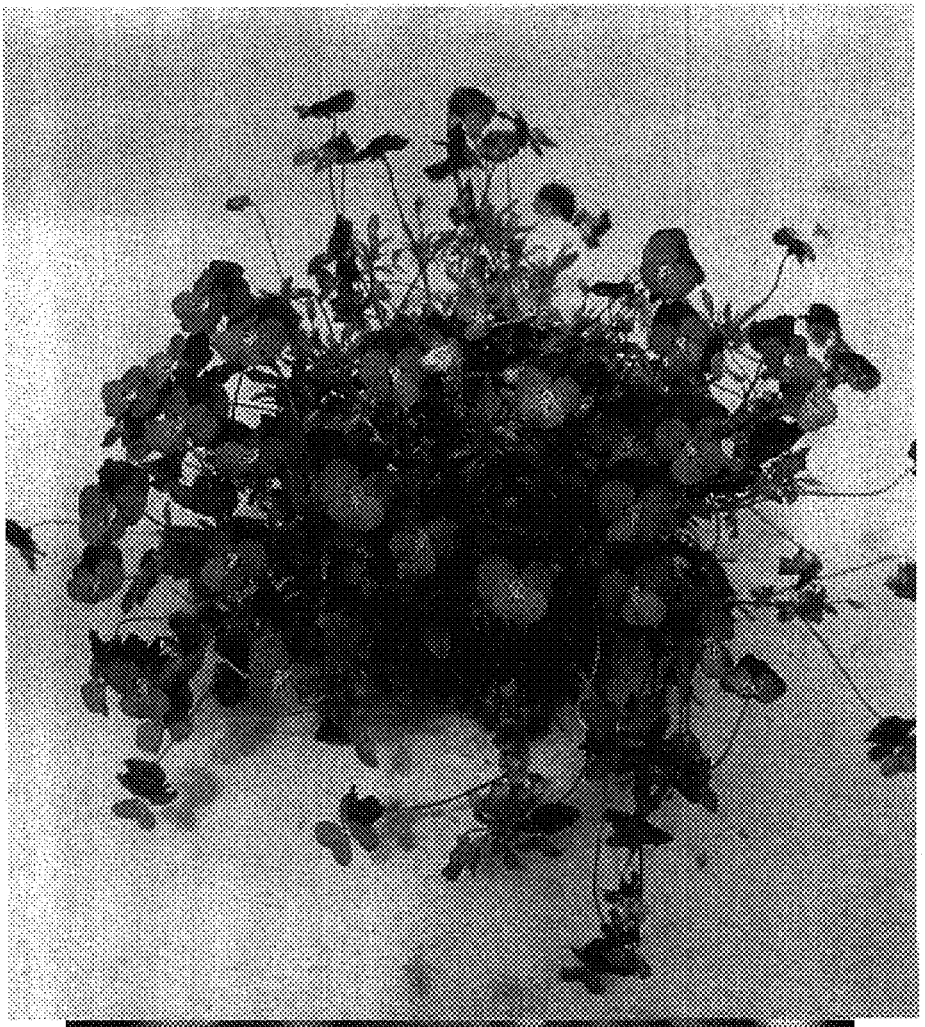
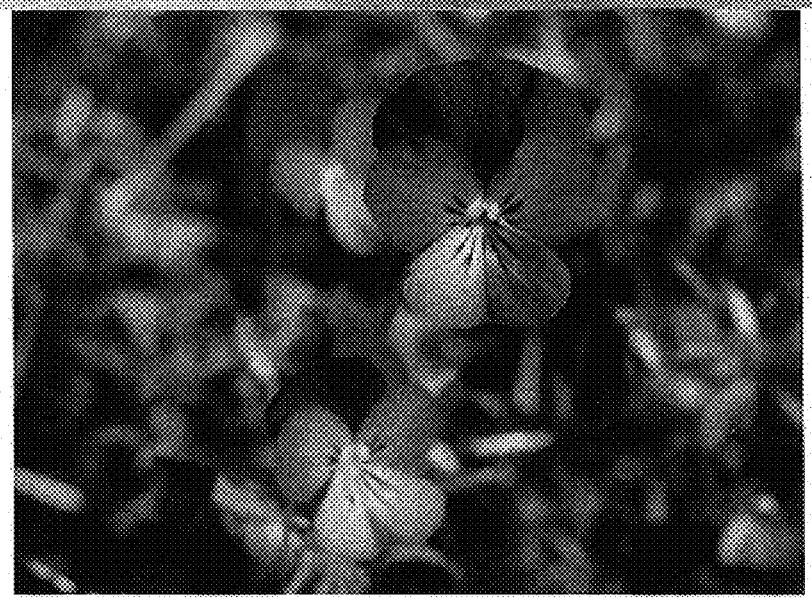

* * * * *